US008481813B2

(12) United States Patent
Eady et al.

(10) Patent No.: US 8,481,813 B2
(45) Date of Patent: Jul. 9, 2013

(54) TRANSFORMATION AND REGENERATION OF ALLIUM PLANTS

(75) Inventors: Colin Charles Eady, Christchurch (NZ); Fernand Othmar Kenel, Christchurch (NZ); Sheree Alma Brinch, Christchurch (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 380 days.

(21) Appl. No.: 12/739,700

(22) PCT Filed: Oct. 24, 2008

(86) PCT No.: PCT/NZ2008/000276
§ 371 (c)(1),
(2), (4) Date: Jul. 16, 2010

(87) PCT Pub. No.: WO2009/054734
PCT Pub. Date: Apr. 30, 2009

(65) Prior Publication Data
US 2010/0281581 A1 Nov. 4, 2010

(30) Foreign Application Priority Data
Oct. 24, 2007 (NZ) ........................................ 562781

(51) Int. Cl.
C12N 15/84 (2006.01)
A01H 4/00 (2006.01)
(52) U.S. Cl.
USPC ........... 800/294; 800/279; 800/300; 800/302; 800/290; 800/282; 800/284; 800/285
(58) Field of Classification Search
None
See application file for complete search history.

(56) References Cited

U.S. PATENT DOCUMENTS
6,380,461 B1  4/2002  Bidney et al.
7,112,720 B1  9/2006  Lister et al.

FOREIGN PATENT DOCUMENTS
CN   101113458 A  * 1/2008
ES   2077181 T3  * 11/1995
WO   99/04012       1/1999
WO   99/46395 A1   9/1999
WO   00/44919 A1   8/2000
WO   00/65903 A1  11/2000
WO   02/44390 A1   6/2002
WO   03/074707 A1  9/2003

OTHER PUBLICATIONS

Eady et al. (Ann. appl. Biol. (2003), 142:213-217).*
Annals of Botany 106: 709-733, 2010, p. 709.*
Bastar et al. (2003) "Use of direct somatic organogenesis for Agrobacterium-mediated transformation of onion" Acta Biologica Slovenica, 46: 3-7.
Eady et al. (2008) "Compendium of Transgenic Crop Plants: Transgenic Vegetable Crops", Blackwell Publishing, Oxford, UK, pp. 186-204.
Aswath et al. (Oct. 7, 2005) "*Agrobacterium* and biolistic transformation of onion using non-antibiotic selection marker phosphomannose isomerase." *Plant Cell Reports* 25: 92-99.
Barandiaran et al. (Sep., 1998) "Biolistic transfer and expression of a *uidA* reporter gene in different tissues of *Allium sativum* L." *Plant Cell Reports* 17: 737-741.
Dommisse et.al. (1990) "Onion is a monocotyledonous host for agrobacterium" *Plant Science* 69: 249-257.
Eady, C. C. (1995) "Towards the transformation of onions." *New Zealand Journal of Crop and Horticultural Science* 23: 239-250.
Eady et al. (1996) "Transient expression of *uidA* constructs in in vitro onion (*Allium cepa* L.) cultures following particle bombardment and *Agrobacterium-mediated* DNA delivery" *Plant Cell Reports* 15: 958-962.
Eady et al. (Mar. 1998) "Somatic embryogenesis and plant regeneration from immature embryo cultures of onion (*Allium cepa* L.)" *Plant Cell Reports* 18: 111-116.
Eady et al. (Mar. 1998) "A comparison of four selective agents for use with *Allium cepa* L. immature embryos and immature embryo-derived cultures" *Plant Cell Reports* 18: 117-121.
Eady et al. (2000) "*Agrobacterium tumefaciens*-mediated transformation and transgenic-plant regeneration of onion (*Allium cepa* L.)." *Plant Cell Reports* 19: 376-381.
Eady et al. (2003) "*Agrobacterium tumefaciens*-mediated transformation and regeneration of herbicide resistant onion (*Allium cepa*) plants." *Annals of Applied Biology* ; 142: 213-217.
Eady et al. (2005). "*Agrobacterium tumefaciens*-mediated transformation of leek (*Allium porrum*) and garlic (*Allium sativum*)." *Plant Cell Reports* 24 (4): 209-15.
Eady et al. (Aug. 2008) "Silencing Onion Lachrymatory Factor Synthase Causes a Significant Change in the Sulfur Secondary Metabolite Profile" *Plant Physiology* 147: 2096-2106.
Fereol et al. (2002) "Evidence of a somatic embryogenesis process for plant regeneration in garlic (*Allium sativum* L.)" *Plant Cell Rep* 21:197-203.
Haseloff et al. (Mar. 1997) "Removal of a cryptic intron and subcellular localization of green fluorescent protein are required to mark transgenic Arabidopsis plants brightly" *Proc. Natl. Acad. Sci. USA* 94(6): 2122-2127.
Hong et al. (May 7, 1995) "Somatic embryogenesis and plant regeneration in garden leek" *Plant Cell Tissue & Organ Culture* 43: 21-28.
International Search Report and Written Opinion, for corresponding WO application No. PCT/NZ2008/000276, Feb. 16, 2009.
International Preliminary Report on Patentability, for corresponding WO application No. PCT/NZ2008/000276, Feb. 15, 2010.

(Continued)

*Primary Examiner* — David T Fox
*Assistant Examiner* — Jared Shapiro
(74) *Attorney, Agent, or Firm* — Lathrop & Gage LLP

(57) ABSTRACT

This invention relates to methods for the transformation of plants from the genus *Allium*, and transformed plants produced according to the method. Specifically, this invention relates to direct transformation of *Allium* leaf tissue using *Agrobacterium* mediated transformation, and plants regenerated from the transformed leaf tissue. In various aspects, the invention relates to a method of obtaining a transformed *Allium* leaf tissue and methods of obtaining a transformed *Allium* plant by regenerating the transformed leaf tissue.

12 Claims, 21 Drawing Sheets

OTHER PUBLICATIONS

Klein et al. (1987) "High-Velocity microprojectiles for delivering nucleic acids into living cells" *Nature* 327: 70-73.

Kondo et al. (2000) "Transformation and regeneration of garlic (*Allium sativum* L.) by *Agrobacterium*-mediated gene transfer." *Plant Cell Reports* 19: 989-993.

Saker (1998) "In vitro regeneration of onion through repetitive somatic embrogenesis" *Biologia Plantarum* 40(4): 499-506.

Simmonds et al. (2004) "Oxalate oxidase; a novel reporter gene for moncot and dicot transformations." *Molecular Breeding* 13(1): 79-91.

Vain et al. (Oct. 1998) "The green fluorescent protein (GFP) as a vital screenable marker in rice transformation" *Theoretical & Applied Genetics* 96: 164-169.

Wilmink et al. (1993) "Selective agents and marker genes for use in transformation of monocotyledonous plants" *Plant Mol. Biol. Reptr*, 11(2): 165-185.

Xue et al. (1997) "Callus Formation and Plantlet Regeneration through In vitro Culture of Immature Embryo and Seedling in Chinese Chive (*Allium tuberosum* Rottler)" *Journal of the Japanese Society for Horticultural Science* 66, 353-358. English Abstract included.

Zheng et al. (2001) "Molecular characterisation of transgenic shallots (*Allium cepa* L.) by adaptor ligation PCR (AL-PCR) and sequencing of genomic DNA flanking T-DNA borders." *Transgenic Research* 10: 237-245.

Zheng et al. (2001) "*Agrobacterium tumefaciens*-mediated transformation of *Allium cepa* L.: the production of transgenic onions and shallots." *Molecular breeding* 7: 101-115.

Zheng et al. (2004) "The development of a reproducible *Agrobacterium tumefaciens* transformation system for garlic (*Allium sativum* L.) and the production of transgenic garlic resistant to beet armyworm (*Spodoptera exigua* Hubner)." *Molecular breeding* 14: 293-307.

Zheng et al. (2005) "Two different *Bacillus thuringiensis* toxin genes confer resistance to beet armyworm (*Spodoptera exigua* Hubner) in transgenic Bt-Shallots (*Allium cepa* L.)" *Transgenic Research* 14: 261-272.

\* cited by examiner

FIGURE 2
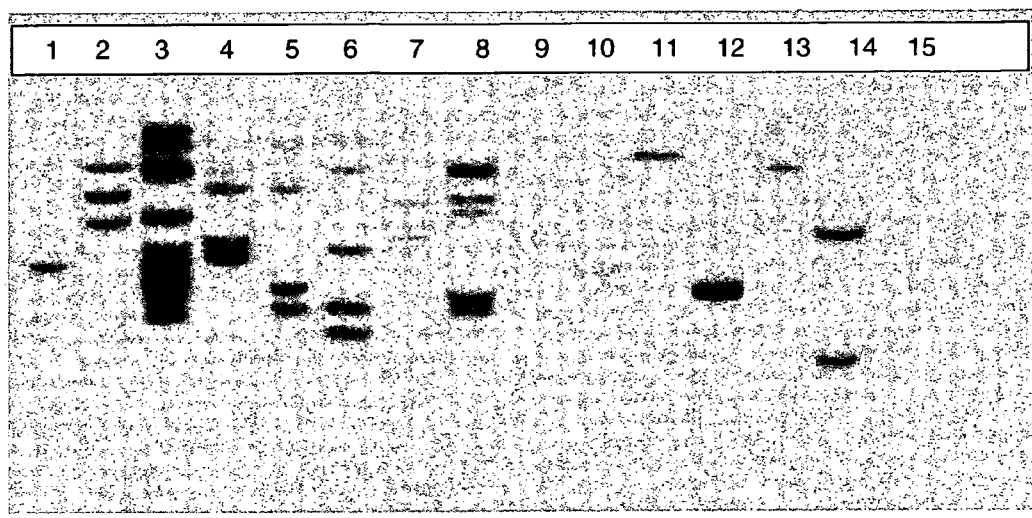
Fig 2a
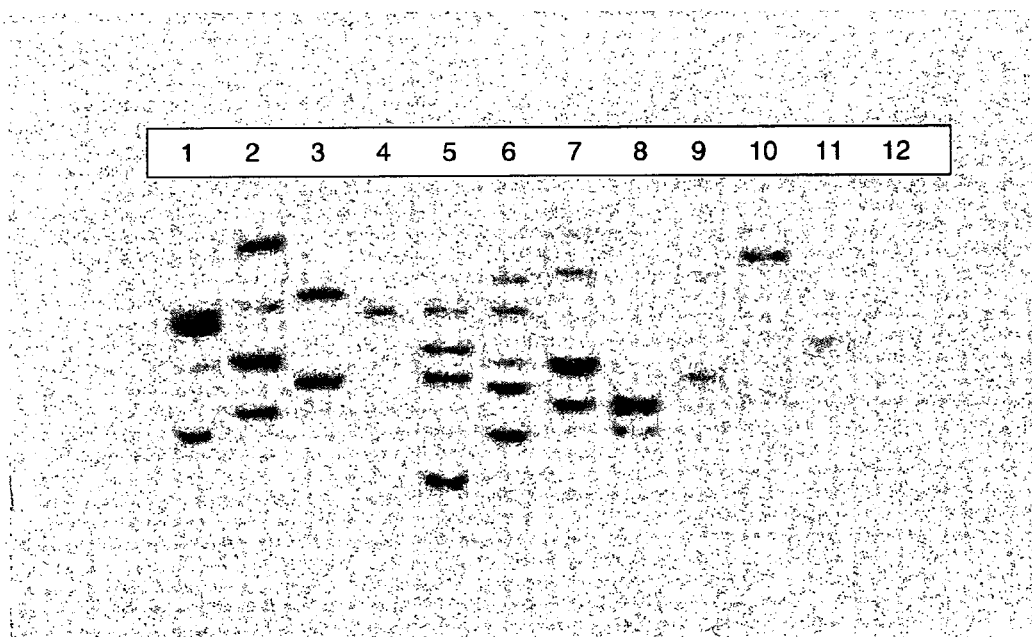
Fig 2b

FIGURE 17
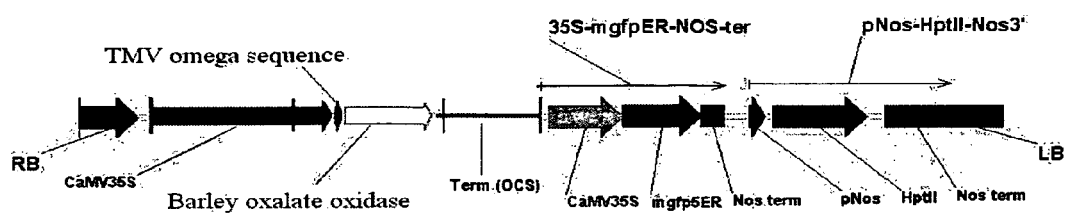
Fig 17a
Fig 17b
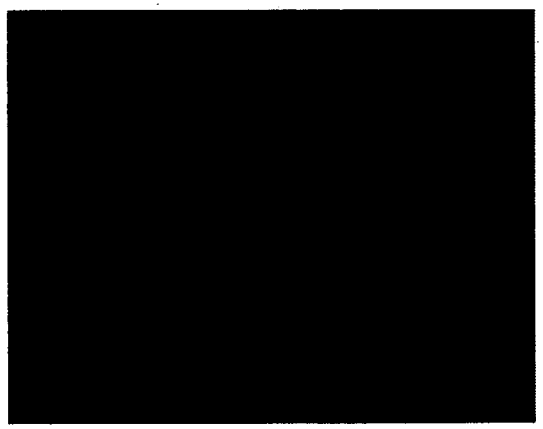
Fig 17c

FIGURE 17 cont.
Fig 17d
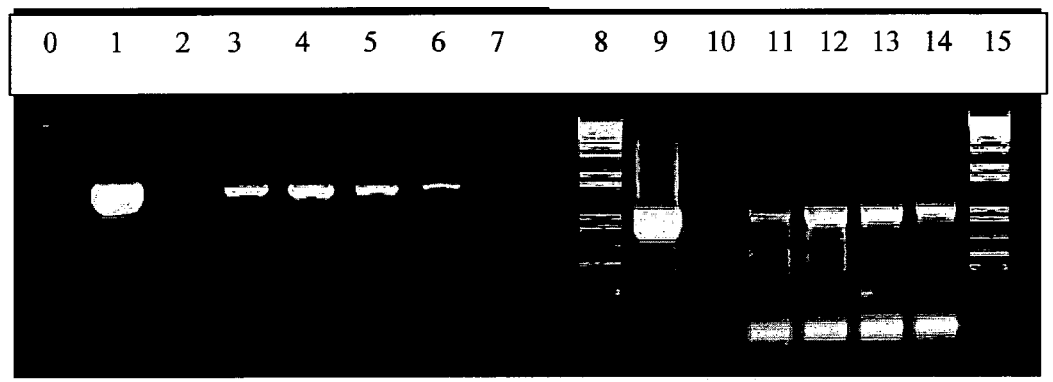
Fig 17e

Figure 18
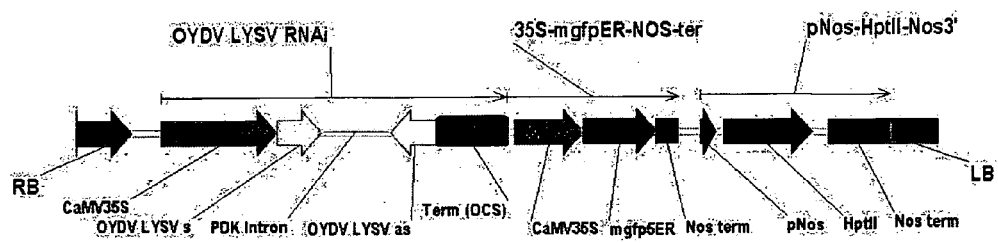
Fig 18a
Fig 18b

```
                           SEQUENCE LISTING

<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: Synthetic construct:  GFPa primer

<400> SEQUENCE: 1
acgtctcgag ctcttaaagc tcatcatg                                        28

<210> SEQ ID NO 2
<211> LENGTH: 29
<212> TYPE: DNA
<213> ORGANISM: Artificial Sequence
<220> FEATURE:
<223> OTHER INFORMATION: Synthetic construct:  GFPb primer

<400> SEQUENCE: 2
acgtctcgag gatccaagga gatataaca                                       29
```

TRANSFORMATION AND REGENERATION OF ALLIUM PLANTS

CROSS REFERENCE TO RELATED APPLICATIONS

This application is filed under 35 U.S.C. 371 as the United States National Stage Application of International Application No. PCT/NZ2008/000276, filed Oct. 24, 2008, which International Application claims benefit of New Zealand Application No. 562781, filed Oct. 24, 2007.

FIELD OF INVENTION

The invention relates to a method of transforming plants of the *Allium* family and to the transformed plants.

BACKGROUND OF THE INVENTION

There are few published protocols for the transformation and regeneration of *Allium* species. The *Allium* crop species are probably the most economically important vegetable species for which transformation technology is still difficult. For other major vegetable crops, efficient transformation systems have been produced.

Initially, many monocotyledons were thought to be unsusceptible to *Agrobacterium*-mediated transformation. The development of direct gene transfer techniques soon led to bombardment being the favoured method of monocotyledon transformation. However, direct gene transfer is not without its problems. Often, low transformation frequencies and a high frequency of unusual integration patterns has been observed in transgenic plants. Recently, *Agrobacterium*-mediated transformation of monocotyledons has gained favour and many monocotyledonous species (including rice, wheat, barley, maize and sugarcane) have now been transformed using this method. A key component in the success of these systems has been the use of highly embryogenic tissue types, and precise post transformation selection protocols.

Recently, Haseloff (1997) has modified the gfp gene to enhance its use as a transgenic marker gene in viable plant systems. Green fluorescent protein (GFP) enables researchers to follow precisely the fate of any cells expressing this gene and so optimise post transformation cell survival. Such a system has been useful in the development of the *allium* transformation protocol reported here.

As monocotyledons, the *Allium* species were predisposed to be recalcitrant to transformation. Onions (*Allium cepa* L) are a crop with diverse environmental requirements. It has, therefore, been relatively understudied with respect to the application of biotechnology. There are only a few reports of DNA delivery to *Alliums* (Klein 1987; Dommisse et al. 1990; Eady et al. 1996; Barandiaran et al. 1998). Three workers used direct gene transfer whilst Dommisse et al. (1990) demonstrated that *Agrobacterium*-mediated transformation may be possible. Some reports of regeneration protocols for *Alliums* that are appropriate for transformation study have become available (Hong and Deberg 1995; Xue et al. 1997; Eady et al. 1998; Saker 1998). Only one report exists on the development of potential selective agents for use in *Allium* transformation (Eady and Lister 1998a).

More recently U.S. Pat. No. 7,112,720 describes a method of transforming onion plants using *Agrobacterium* mediated transformation and using immature embryos as the explant source. Since then, there have been several further reports of transformation of onion (Zheng et al. 2001b; Baster et al. 2003; Aswath et al. 2006), leek (Eady et al. 2005) and garlic (Kondo et al. 2000; Eady et al. 2005). However, all of these reports are inefficient and based around immature embryo use (e.g. all previous Eady et al. transformations) or the use of floral tissue (Bastar et al 2003) or callus derived from seedling radicle tissue (Aswath et al 2006) or mature zygotic embryo callus (Zheng et al 2001), or callus derived from meristamatic shoot primordia (Kondo et al 2000). None of the protocols thus far developed have used direct regeneration from immature leaf tissue as outlined in this invention.

To date leaf tissue has not been used as, or considered a viable, source of tissue for *Allium* transformation. Leaf tissue has not been investigated or considered a useful starting material due to difficulties in getting good transformation of leaf tissue. Furthermore, leaf cells from monocotyledons are notoriously recalcitrant to regeneration, unlike dicotyledonous leaf tissue which is often very easily regenerated. There are no reports of successful direct regeneration from isolated *allium* leaf tissue and only low frequency regeneration from twin scales, in which a few cells on the abdaxial side of the upper leaf in the twin scale regenerates (reviewed by Eady 1995 updated in Eady and Hunger 2008). There has been one recent report of regeneration from garlic leaf via callus and somatic embryogenesis (Fereol et al. 2002). The identification in this work of 'plastic' immature leaf cell types from the leaf base of *allium* species and their use for transformation and regeneration is an unexpected and novel finding that can greatly enhance the application of biotechnology to crop *allium* species.

OBJECT OF THE INVENTION

It is an object of the invention to provide a method of transforming *allium* plants or to at least provide the public with a useful choice.

SUMMARY OF THE INVENTION

The invention provides a method of transforming plants of the *Allium* genus comprising inoculating a leaf tissue of an *Allium* species with an *Agrobacterium tumefaciens* strain containing a suitable vector or plasmid and then selectively regenerating the *allium* cells that have integrated the DNA sequence.

Specifically the present invention provides for a method of transforming cells from an *Allium* plant species with a polynucleotide of interest comprising the steps of:
  (i) isolating a section of leaf from the *Allium* plant to be transformed;
  (ii) co-culturing the section of leaf with *Agrobacterium* containing one or more suitable vectors comprising the polynucleotide of interest for a length, of time sufficient to achieve transfer of the polynucleotide sequence of interest into one or more plant leaf cells; and
  (ii) transferring the section of leaf to a selection medium that allows for the selection of transformed *Allium* plant cells.

The leaf pieces are preferably transformed with a binary vector. More preferably the leaf pieces of an *Allium* species are inoculated prior to their differentiation into tissue cultures. However, the leaf pieces of an *Allium* species may be inoculated immediately following their isolation. Preferably immature leaf pieces are used. Further, the selection medium includes an agent to selectively kill the *Agrobacterium*.

The method according to the present invention suitable for use with any *Allium* plant, more specifically the *Allium* plant is any one of *Allium cepa, Allium fistulosum* or *Allium ampeloprasum, Allium ascalonicum, Allium schoenoprasum* or *Allium sativum*.

The transformed *Allium* cells may also be used to generate whole plant. Therefore, the method of the present invention can also comprising the step of regenerating a plant from the transformed cells.

According to another aspect the invention provides an *Allium* plant transformed by the method according the method of the present invention. The *Allium* plant can be transformed with a polynucleotide of interest that confers an agronomic advantage. For example; resistance to herbicides, such as glyphosate and or phosphinothricin; resistance to fungal disease, such as Allium white rot; resistance to virus diseases, such as Iris Yellow Spot Virus or the viruses responsible for garlic mosaic disease; resistance to bacterial diseases; resistance to insect pests such as onion maggot and or thrips.

Alternatively, the *Allium* plant can be transformed with a polynucleotide of interest that confers a modification of the bolting and flowering pathway. For example florigen level, recognition or activity.

Alternatively, the *Allium* plant can be transformed with a polynucleotide of interest that confers a quality trait advantage. For example; overexpression or silencing of colour pathway genes or their regulators or, the polynucleotide of interest confers overexpression or silencing of sulphur pathway genes or their regulators, for example the silencing of the lfs gene through the use of lfs RNAi sequences; or the overexpression or silencing of Carbohydrate pathway genes or their regulators for example the sst1 gene or sst1 RNAi sequences.

BRIEF DESCRIPTION OF THE DRAWINGS

The invention will now be described by way of example only and with reference to the following drawings in which.

Figure 1:
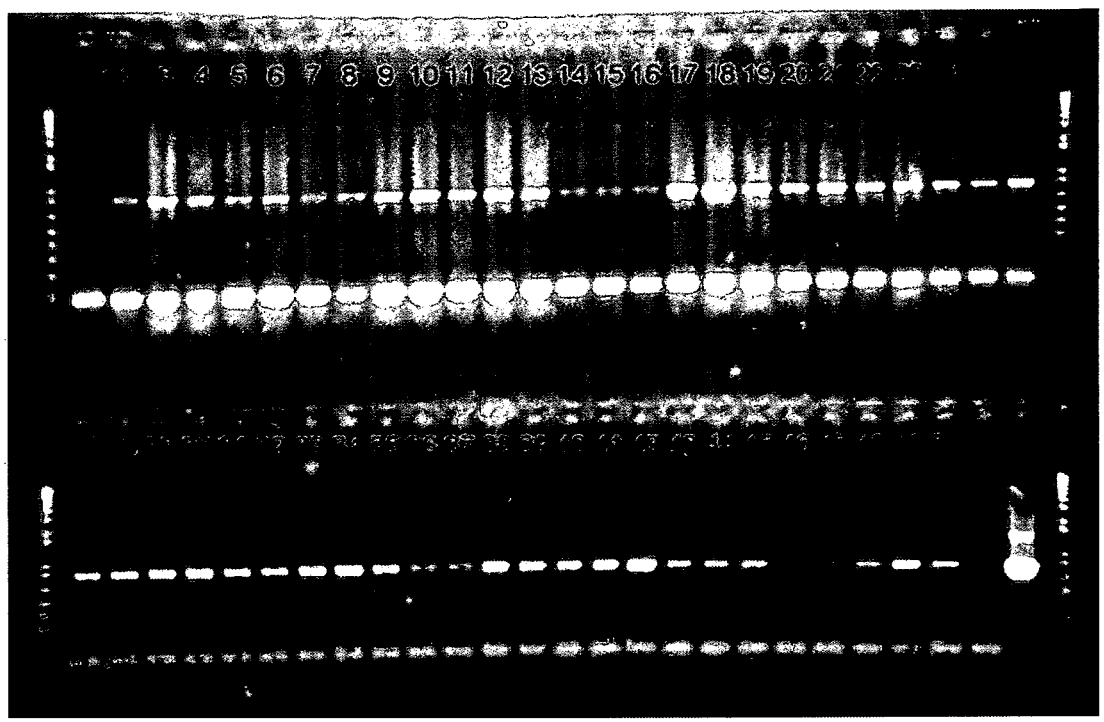
FIG. 1 is PCR analysis for the GFP gene in transgenic Garlic in the greenhouse (Lab-book ref: 110967). Samples: 1(Blank), 2-10 (0629 16 C), 11-14 (0629 21 B), 15 (0630 6 A), 16 (0631 5 G), 17-18 (0631 8 B), 19-41 (0631 11 E), 42-43 (0631 17 F), 44-45 (0631 18 B), 46 (0631 18 Q), 47-50 (0631 19 A), 51 Non Transgenic Garlic, 52 pART27H mGFP5-ER plasmid. (Numbers in brackets refer to separate garlic transgenic events.)

PCR conditions: 0.5 uM GFPa & b primers, 2 mM $Mg^{2+}$, 40 cycles (94° C. 1 min, 60° C. 1 min, 72° C. 1 min). Primers sequences

```
(GFPa: SEQ ID NO: 1: ACGTCTCGAGCT
CTTAAAGCTCATCATG)

(GFPb: SEQ ID NO: 2: ACGTCTCGAGGA
TCCAAGGAGATATAACA).
```

FIG. 2. shows the results from Southern blot probing for the gfp gene in transgenic *Allium sativum* plants transformed with pART27H-mgfp-ER. In FIG. 2a: Lane 1: 0630 6(A); lane 2: 0631 2(C); lane 3: 0631 2(G); lane 4: 0631 5(A); lane 5: 0631 8(A); lane 6: 0631 8(B); lane 7: 0631 8(I); lane 8: 0631 8(M); lane 9: 0631 11(B); lane 10: 0631 11(E); lane 11: 0631 17(B); lane 12: 0631 17(I); lane 13: 0631 17(N); lane 14: 0631 18(B); lane 15: non-transgenic garlic control. In FIG. 2b, Lane 1: 0631 18(F); lane 2: 0631 18(I); lane 3: 0631 18(K); lane 4: 0631 18(Q); lane 5: 0631 20(A); lane 6: 0631 20(E); lane 7: 0631 20(F); lane 8; 0631 21(B); lane 9: 0631 22(B); lane 10: 0631 23(A); lane 11: 0631 24(B); lane 12: non-transgenic garlic control.

Figure 3:

FIG. 3 is an onion (*A. cepa*) inner immature leaf 1 week after cocultivation showing GFP expression.

Figure 4:

FIG. 4 is an onion (*A. cepa*) outer immature leaf 11 days after cocultivation showing multicellular GFP expression.

Figure 5:
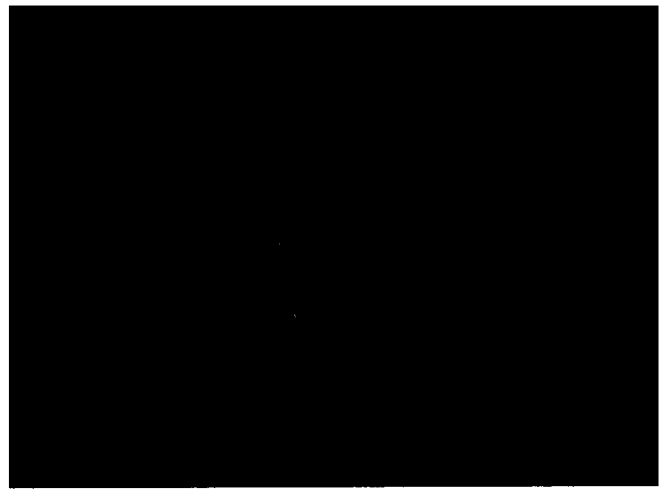

FIG. 5 is an onion (*A. cepa*) nodular culture 13 weeks after cocultivation showing GFP expression.

Figure 6:
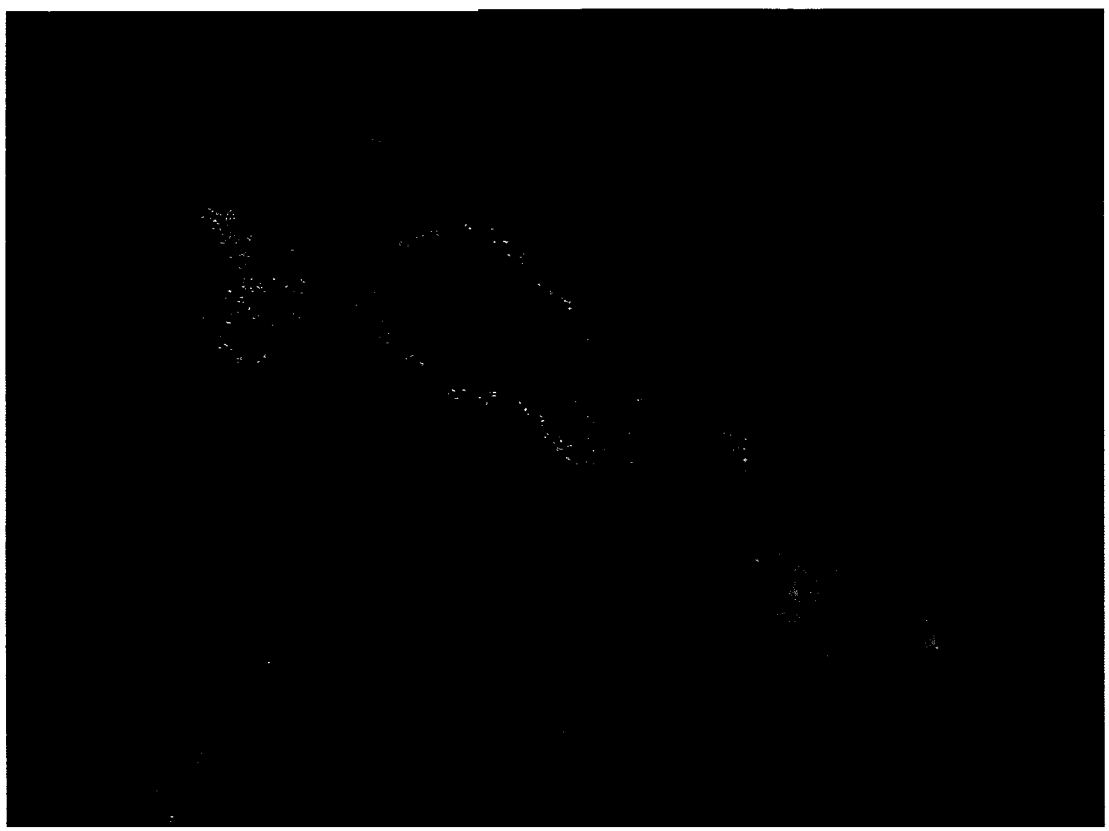
Figure 7:
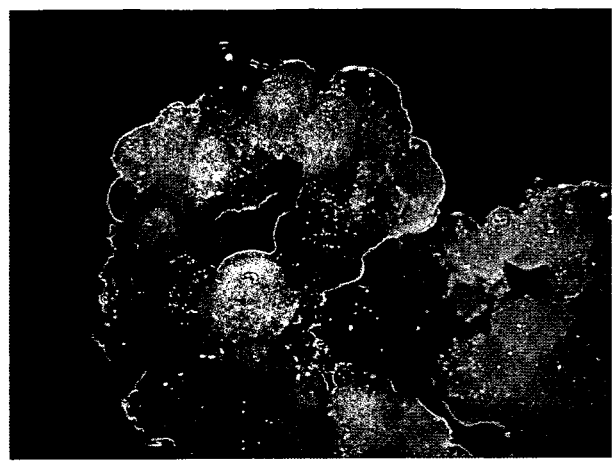

FIG. 6 is an onion (*A. cepa*) regenerating culture from transformed immature leaf tissue 4 months after cocultivation showing GFP expression FIG. 7 is a nodular culture formed from immature onion (*A. cepa*) leaves.

Figure 8:

FIG. 8 shows regenerating shoots from onion (*A. cepa*) immature leaves cultured on a modified P5 media containing 4-FPA on modified P5 media containing 4-FPA, one month after transfer to SM4 regeneration medium.

Figure 9:
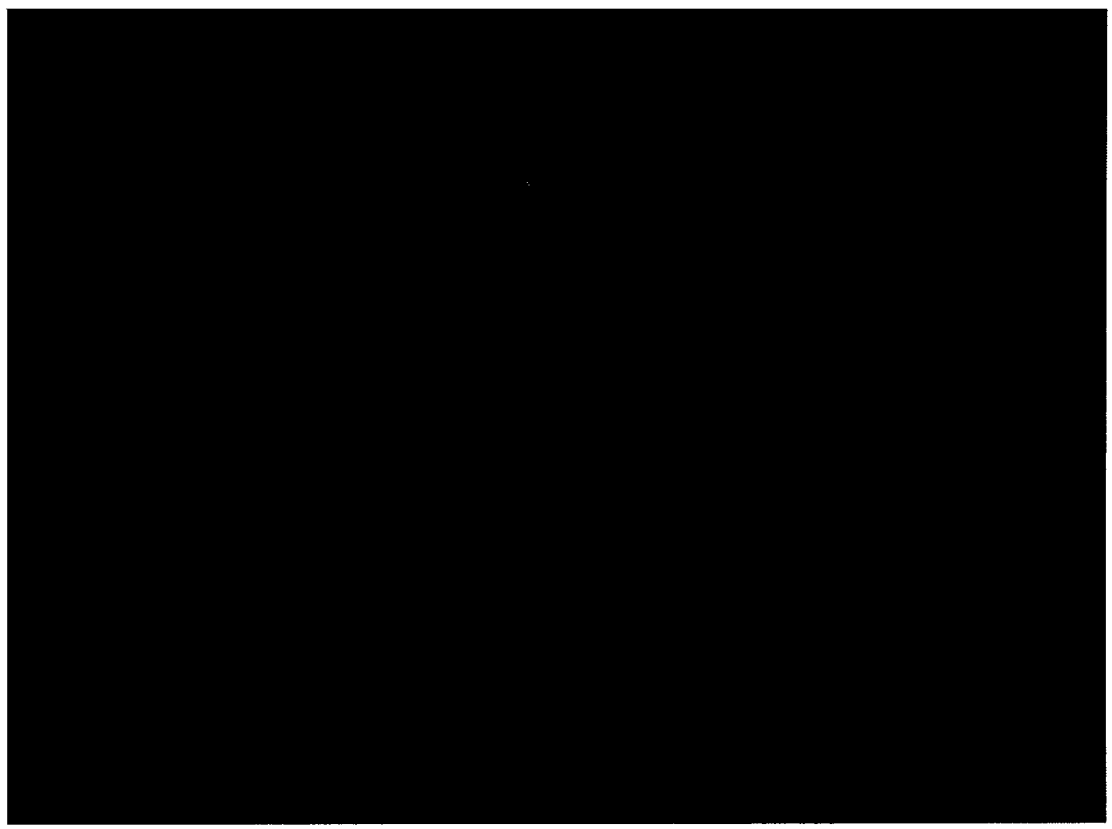

FIG. 9 is a spring onion (*A. fistulosum*) immature leaves exhibiting GFP expression 12 days after cocultivation.

Figure 10:
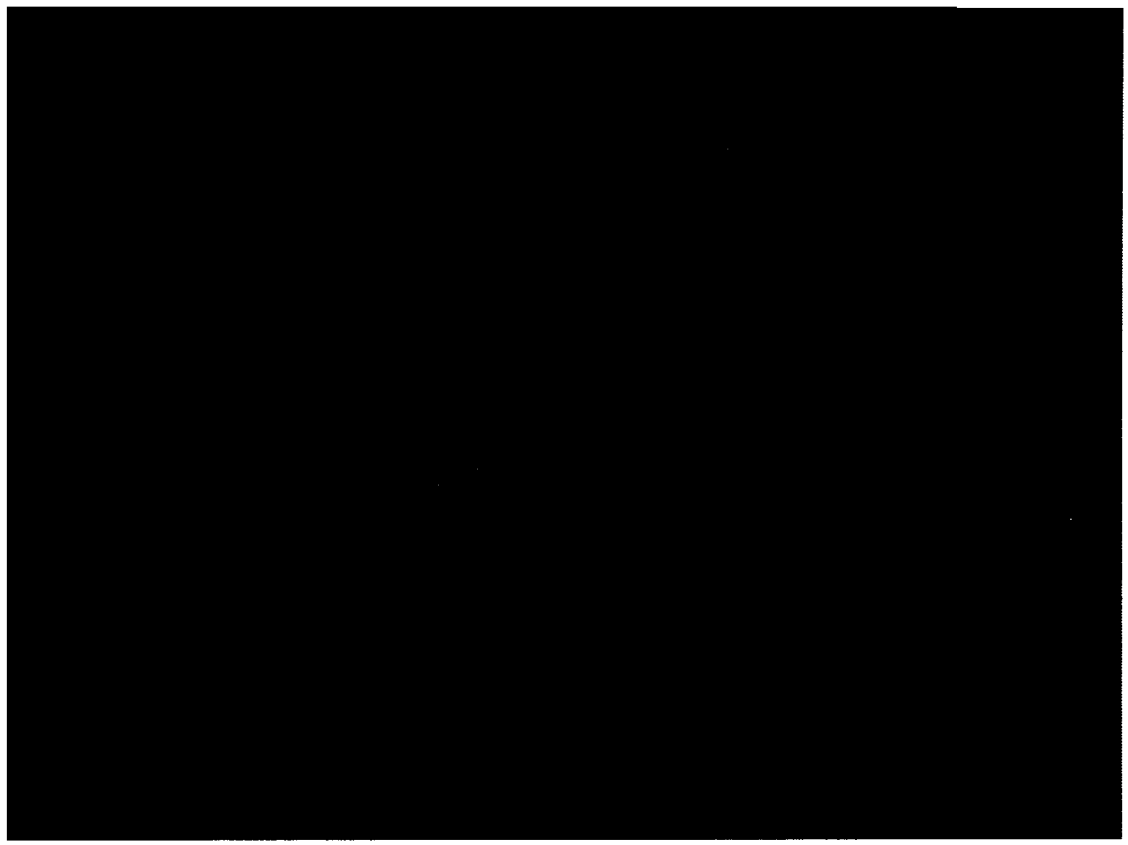

FIG. 10 is a spring onion (*A. fistulosum*) immature leaves exhibiting multicellular GFP tissue 21 days after cocultivation.

Figure 11:
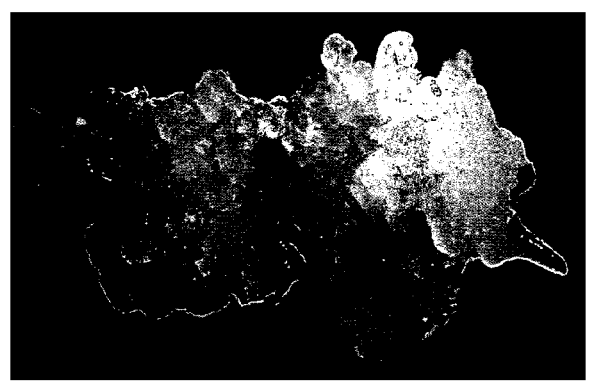

FIG. 11 is a nodular culture with embryogenic structures forming from Spring onion (*A. fistulosum*) immature leaves after 12 weeks of culture on a modified P5 medium containing 4-FPA and BA.

Figure 12:
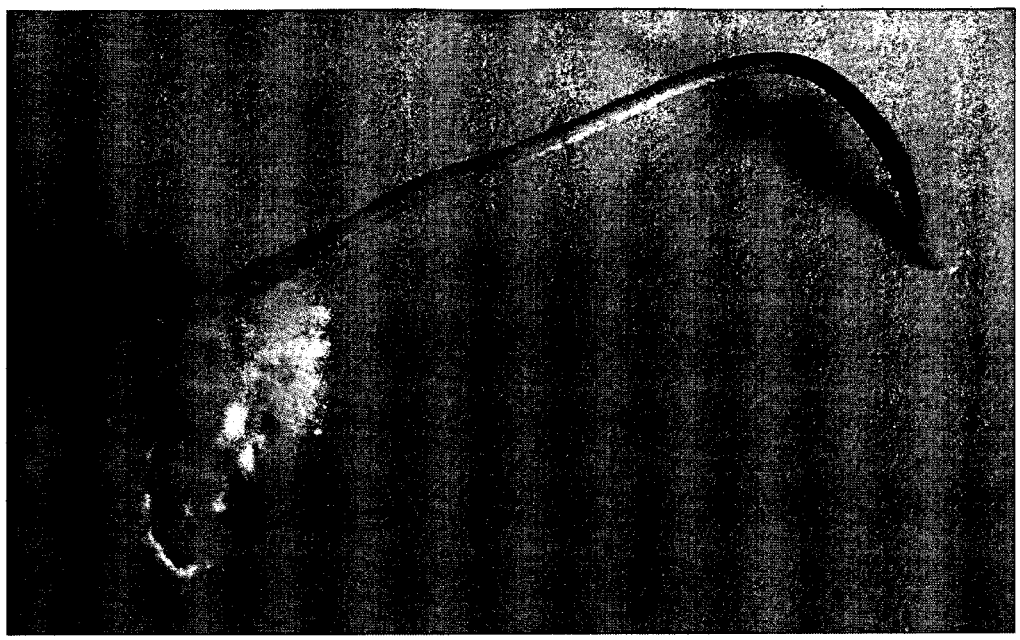

FIG. 12 is a regenerating shoot from a spring onion (*A. fistulosum*) immature leaf cultured on a modified P5 media containing 4-FPA, 4 days after transfer to SM4 regeneration media.

Figure 13:

FIG. 13 is a leek leaf exhibiting GFP expression 8 days after cocultivation.

Figures 14, 14A:
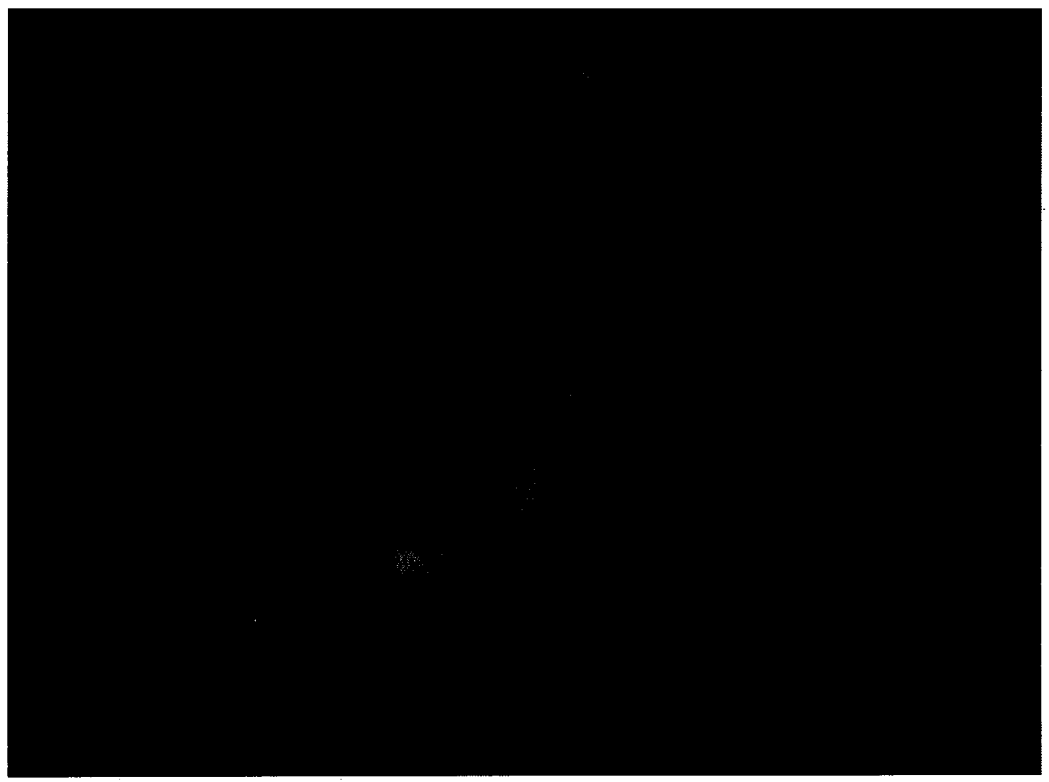
Figures 14, 14B:
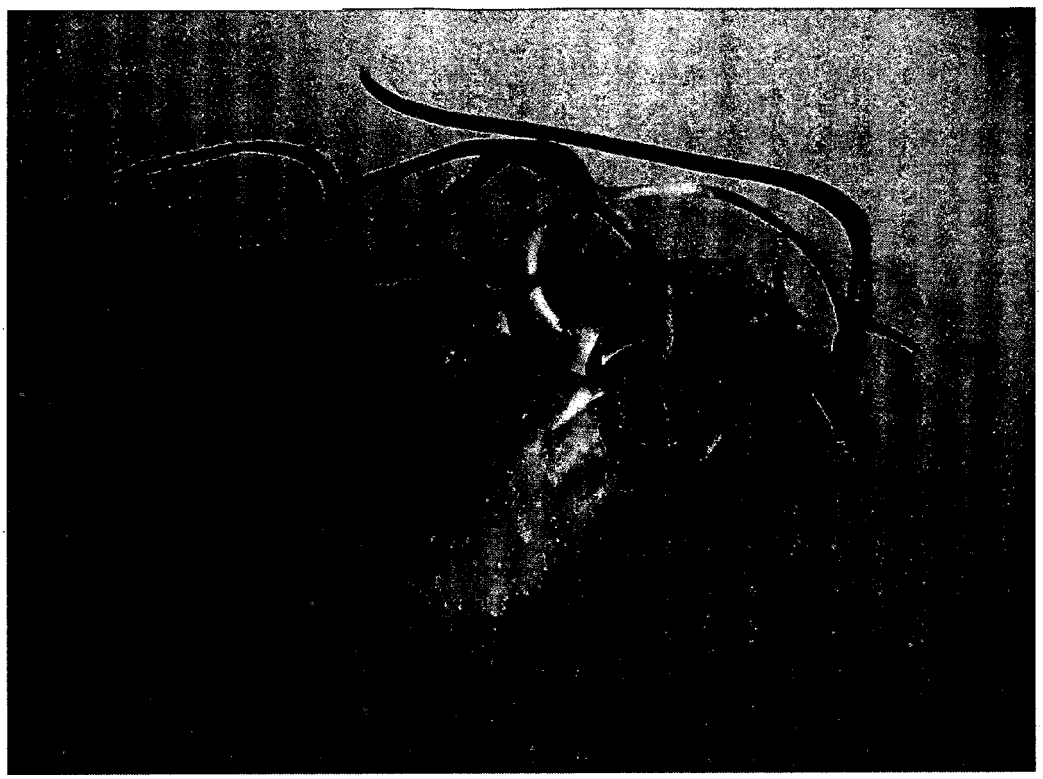
Figure 15:

FIG. 14, FIG. 14a shows Leek nodular embryogenic cultures from a immature leaf transformation showing GFP immature embryo structures. FIG. 14b shows Leek shoot cultures regenerating from immature leaf cultures 1 month after transfer to SM4 medium FIG. 15 is a garlic leaf tissue 10 days (top left), 3 weeks (top right) and 2 months (bottom left) after co-cultivation with *Agrobacterium* containing the binary vector pArt27 m-gfp-ER.

Figure 16:
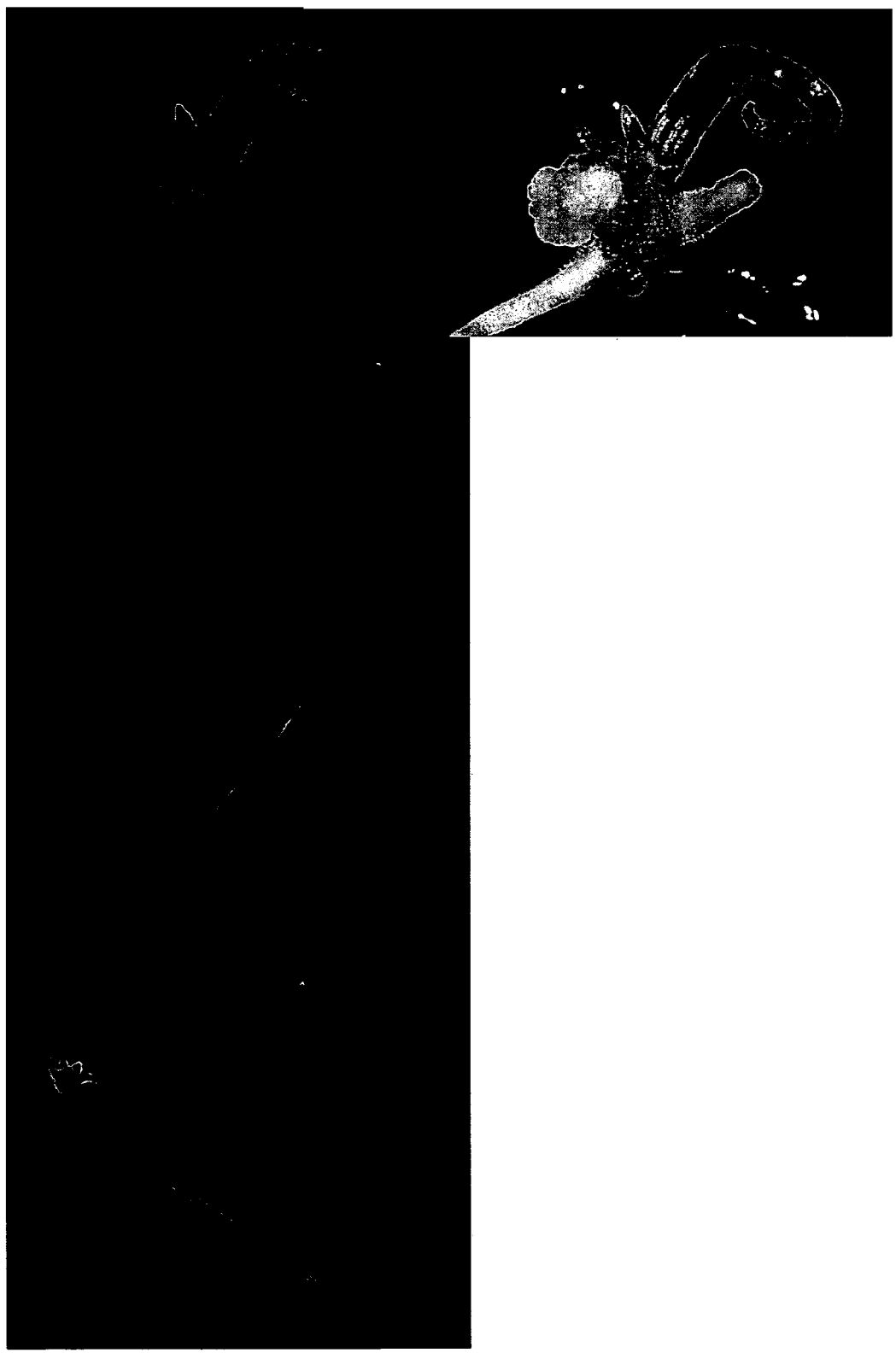

FIG. 16 shows regenerating garlic plants containing the gfp reporter gene. Top left light photo of shoot culture, top right photo under blue light excitation showing green fluorescence. Bottom, composite of whole garlic plant under blue light excitation showing green fluorescence indicating integration and expression of the gfp reporter gene.

Figures 18, 18C:
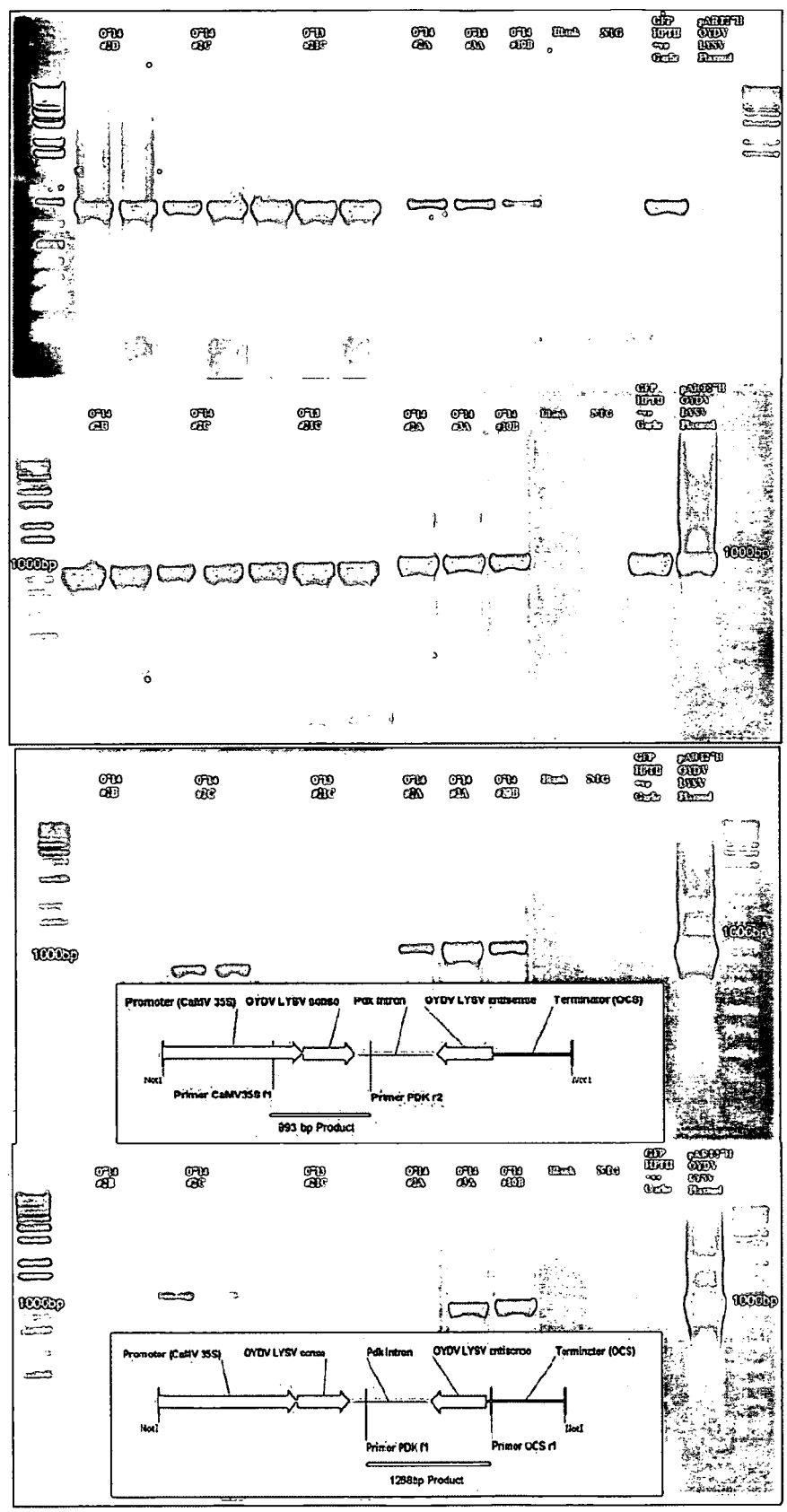

FIG. 17 shows the transformation of Garlic with fungal resistance genes. FIG. 17a shows the T-DNA construct transformed into garlic using the immature leaf transformation system to confer reporter gene expression, antibiotic resistance and oxalate oxidase activity in order to confer resistance to certain fungal pathogens. FIG. 17b shows the regenerated transformed garlic plants, regenerated from transformed leaf tissue. FIG. 17c shows GFP expression in the regenerated plant tissue. FIG. 17d shows histochemical analysis of oxalate oxidase activity in transgenic garlic. Black staining indicates enzyme activity (stain taken up from cut site of leaf, hence not all tissue is stained). FIG. 17e shows molecular analysis of oxalate oxidase transgene integration in garlic. Left lanes 1-7 amplified GFP reporter transgene region in four transgenic garlic lines. Right lanes 8-15 amplified hygromycin selector transgene region in four transgenic garlic lines. Lanes 1 and 9 plasmid positive control. Lane 2 and 10 genomic *allium* DNA (negative control). Lanes 3-6 and 11-14 DNA from transgenic garlic plants 0818 1E, 7b, 0819 5a, and 0821 6d respectively. Lanes 0,7,8, and 15 marker DNA. Amplified fragments for the GFP gene are a 833 bp fragment, and a 1100 bp for the hygromycin gene fragment FIG. 18 shows the transformation of Garlic with viral resistance genes. FIG. 18a shows the T-DNA construct transformed into garlic using the immature leaf transformation system to confer reporter gene expression, antibiotic resistance and resistance to the potyviruses OYDV and LYSV in order to confer tolerance to Garlic Mosaic Disease. FIG. 18b shows transgenic garlic plants from immature leaf transformation using the T-DNA construct in FIG. 18a growing in a PC2 glasshouse after selection on the antibiotic hygromycin. FIG. 18c shows PCR analysis of 6 lines (0714 #2B, #2C, #2A, #3A, #10B and 0713 #21C) regenerated from immature leaf transformation using the T-DNA construct outlined in FIG. 18a. Top gel shows amplification products for a 833 bp gfp gene fragment, second gel shows amplification products for a 1100 bp hygromycin gene fragment. The third gel shows amplification products for a 993 bp sense fragment of the RNAi construct and the fourth gel show amplification products for a 1268 bp intron and antisense fragment of the RNAi construct. Three lines 0714 #2C, #3A and #10B were recovered and shown to contain all components of the T-DNA construct.

DEFINITIONS

Before describing embodiments of the invention in detail, it will be useful to provide some definitions of terms used herein.

The term "expression" includes production of polynucleotides and polypeptides, in particular, the production of RNA (e.g., mRNA) from a gene or portion of a gene, and includes the production of a protein encoded by an RNA or gene or portion of a gene, and the appearance of a detectable material associated with expression. For example, the formation of a complex, for example, from a protein-protein interaction, protein-nucleotide interaction, or the like, is included within the scope of the term "expression". Another example is the binding of a binding ligand, such as a hybridization probe or antibody, to a gene or other oligonucleotide, a protein or a protein fragment and the visualization of the binding ligand. Thus, increased intensity of a spot on a microarray, on a hybridization blot such as a Northern blot, or on an immunoblot such as a Western blot, or on a bead array, or by PCR analysis, is included within the term "expression" of the underlying biological molecule.

The term "isolated" refers to something that has been separated from it's natural environment.

The term "oligonucleotide" refers to a polynucleotide, typically a probe or primer, including, without limitation, single-stranded deoxyribonucleotides, single- or double-stranded ribonucleotides, RNA:DNA hybrids, and double-stranded DNAs. Oligonucleotides, such as single-stranded DNA probe oligonucleotides, are often synthesized by chemical methods, for example using automated oligonucleotide synthesizers that are commercially available, or by a variety of other methods, including in vitro expression systems, recombinant techniques, and expression in cells and organisms.

The term "plant" refers to any whole plant, or any part thereof, including plant cells, seeds and any organ, such as roots leaves, stems and the like, or any progeny thereof. It also includes both monocotyledons and dicotyledons, and in particular includes any plant from the genus *Allium*.

The term "polynucleotide," when used in the singular or plural, generally refers to any polyribonucleotide or polydeoxyribonucleotide, which may be unmodified RNA or DNA or modified RNA or DNA. This includes, without limitation, single- and double-stranded DNA, DNA including single- and double-stranded regions, single- and double-stranded RNA, and RNA including single- and double-stranded regions, hybrid molecules comprising DNA and RNA, that may be single-stranded or, more typically, double-stranded or include single- and double-stranded regions. Also included are triple-stranded regions comprising RNA or DNA or both RNA and DNA. Specifically included are mRNAs, cDNAs, and genomic DNAs. The term includes DNAs and RNAs that contain one or more modified bases, such as tritiated bases, or unusual bases, such as inosine. The polynucleotides of the invention can encompass coding or non-coding sequences, or sense or antisense sequences.

"Polypeptide," as used herein, refers to an oligopeptide, peptide, or protein sequence, or fragment thereof, and to naturally occurring, recombinant, synthetic, or semi-synthetic molecules. Where "polypeptide" is recited herein to refer to an amino acid sequence of a naturally occurring protein molecule, "polypeptide" and like terms, are not meant to limit the amino acid sequence to the complete, native amino acid sequence for the full-length molecule. It will be understood that each reference to a "polypeptide" or like term, herein, will include the full-length sequence, as well as any fragments, derivatives, or variants thereof.

The term "transformation", refers to the technique of transferring foreign polynucleotide material into cell, The polynucleotide generally is incorporated into the host genome resulting in stable genetic inheritance of the foreign polynucleotide. Cells or organisms containing the foreign polynucleotide are referred to as "transformed" or "transgenic" or "recombinant".

The term "vector" refers to a nucleic acid molecule capable of transporting another nucleic acid to which it has been linked, particularly from one cell to another. One type of vector is an episome, i.e., a nucleic acid capable of extra-chromosomal replication. Another type of vector is an integrative vector that is designed to recombine with the genetic material of a host cell. Vectors may be both autonomously replicating and integrative, and the properties of a vector may differ depending on the cellular context (i.e., a vector may be autonomously replicating in one host cell type and purely integrative in another host cell type). Vectors capable of directing the expression of expressible nucleic acids to which they are operatively linked are referred to herein as "expression vectors."

The practice of the present invention will employ, unless otherwise indicated, conventional techniques of molecular and plant biology (including recombinant techniques), microbiology, cell biology, and biochemistry, which are within the skill of the art. Such techniques are explained fully in the literature, such as, Molecular Cloning: A Laboratory Manual, 2nd edition, Sambrook et al., 1989; Oligonucleotide Synthesis, M J Gait, ed., 1984; Animal Cell Culture, R. I. Freshney, ed., 1987; Methods in Enzymology, Academic Press, Inc.; Handbook of Experimental Immunology, 4th edition, D. M. Weir & C C. Blackwell, eds., Blackwell Science Inc., 1987; Gene Transfer Vectors for Mammalian Cells, J. M. Miller & M. P. Calos, eds., 1987; Current Protocols in Molecular Biology, F. M. Ausubel et al., eds., 1987; and PCR: The Polymerase Chain Reaction, Mullis et al., eds., 1994; Maniatis et al., Molecular Cloning: A Laboratory manual, Cold Spring Harbor Laboratory Press, New York (1982); Sambrook and Russell, Molecular Cloning: A Laboratory manual, 3.sup.rd Edition, Cold Spring Harbor Laboratory Press, New York (2001); Ausubel et al., Current Protocols in Molecular Biology, John Wiley and Sons, New York (1992); Methods in Plant Molecular Biology, Maliga et al, Eds., Cold Spring Harbor Laboratory Press, New York (1995); *Arabidopsis*, Meyerowitz et al, Eds., Cold Spring Harbor Laboratory Press; New york (1994); *Arabidopsis* protocols, J. M Matinez-Zapater and J. Salinas, Eds., Human Press, Totowa, N.J., USA (2001) and the various references cited therein.

DETAILED DESCRIPTION OF THE INVENTION

The invention provides for a method of stably transforming plants of the genus *Allium*. More specifically the invention provides for a method of directly transforming leaf material of plants from the genus *Allium*. *Allium* plants have typically been difficult to transform and to date no one has been able to successfully directly transform leaf material from *Allium* plants. It has been surprisingly found that *Allium* plant tissue can be directly transformed using *Agrobacterium* mediated transformation, and the transformed cells can in turn be used to regenerate transformed *Allium* plants.

The first step of the method according to the present invention is to prepare a section of leaf from an *Allium* plant. Any section of leaf material could be used, however, preferably the leaf material is obtained from immature leaf sections and further preferably from the innermost leaves closest to the basal plate (approximately a 1.5 cm$^3$ of the central base leaf tissue) of immature leaf section obtained from an *Allium* plant preferably following the dormant stage of the lifecycle.

The leaf sections are them prepared for transformation. Preferably this involves sterilizing the tissue and sectioning the leaf into thin slices, for example less than 2 mm thickness, or even more preferably less than 1 mm thickness. This can be achieved using a sterile scalpel or any appropriate sectioning device.

Transfer of a foreign polynucleotide sequence into the genome of the leaf cells is achieved via transformation with *Agrobacterium*. The technique of *Agrobacterium* mediated transformation is a well known and established technique. The system was developed from the natural from of plant transformation that results in crown gall disease. Briefly, in crown gall disease *Agrobacterium tumefaciens* uses a naturally occurring tumor inducing (Ti) plasmid to transfer a piece of DNA replicated from the plasmid called the T-DNA. The genes in the naturally occurring T-DNA result in the formation of galls on the plant at the site of infection. The T-DNA sequence also typically codes for proteins that result in the production of specific amino acids that are metabolized by the *Agrobacterium*, but not the plant.

This system has been utilized for the transformation of plants utilizing polynucleotides of interest. The Ti plasmids have been engineered specifically for transformation purposes. For example, Ti plasmids have been engineered to remove the oncogenes from the T-DNA sequence that result in the tumor formation and these have been replaced by cloning cassettes for the introduction of the polynucleotide of interest, promoters to drive the expression of the polynucleotide of interest, and also to include selection markers. Replication genes are also often, added to allow for the replication of the plasmid in non-*Agrobacterium* hosts. The virulence (Vir) genes required for the ability of the *Agrobacterium* to be able to transform a plant cell have also been separated onto a separate plasmid distinct from the plasmid containing the polynucleotide of interest, which is commonly termed a binary vector.

There are many Ti plasmids and binary vectors available for use in *Agrobacterium* mediated transformation. A person skilled in the art would be able to select a suitable plasmid and insert the polynucleotide of interested and carry the transformation process according to well know methodologies.

The method of the present invention is suitable for use in the transformation of *Allium* plants cells with any polynucleotide of interest. For example, but not limited to, the polynucleotide of interest could confer an agronomic advantage e.g. resistance to herbicides such as glyphosate and or phosphinothricin as demonstrated in onion previously using a immature embryo based transformation system (Eady et al 2003). Resistance to fungal disease such as Allium white rot. Resistance to virus diseases such as Iris Yellow Spot Virus or the viruses responsible for garlic mosaic disease. Resistance to bacterial diseases. Resistance to insect pests, as demonstrated in onion previously using mature zygotic embryo callus (Zheng et al 2004), such as onion maggot and or thrips. The modification of the bolting and flowering pathway by use of polynucleotide sequences that can affect florigen level, recognition or activity.

Alternatively polynucleotide of interest could confer a quality trait advantage e.g. the overexpression or silencing of colour pathway genes or their regulators. The overexpression or silencing of sulphur pathway genes or their regulators, for example the silencing of the lfs gene through the use of lfs RNAi sequences. The overexpression or silencing of Carbohydrate pathway genes or their regulators for example the overexpression of the sst1 gene the silencing through the use of sst1 RNAi sequences.

The polynucleotide of interest is inserted into a suitable vector and the *Agrobacterium* prepared using techniques well known in the art. Preferably this includes the use of acetosyringone in the final proliferation media to enhance vir gene activity. The *Agrobacterium* is then inoculated onto the leaf pieces, by preferably rinsing and resuspending the agrobacteria in liquid plant media containing no antibiotics and acetosyringone (e.g. Eady et al 2000) at a optical density of between 0.1 and 0.9 at 520 nm and then immersing the leaf pieces in this liquid. Preferably, approximately 10 to 20 slices of leaf material are mixed with ~1.5 ml of agrobacteria in a eppendorf. Inoculation is preferably enhanced by a brief vortex of the tissue and agrobacteria followed by vacuum infiltration for 30 minutes. After this inoculation period excess agrobacteria is removed and preferably the tissue is blotted dry on filter paper until all excess liquid is removed.

Following inoculation leaf pieces are co-cultivated using techniques well known in the art with prepared sections of leaf for a length of time sufficient to achieve transfer of the polynucleotide sequence of interest into one or more plant leaf cells. Preferably leaf pieces are placed onto P5 media (Eady et al 2000) and co-cultivated for 3 to 7 days in the dark at 28° C. The method of the present invention is suitable for use of any plant of the *Allium* genus. It will therefore be appreciated that the T-DNA, vector, agrobacteria, inoculation, cocultivation and media conditions required to achieve satisfactory transfer may vary due to factors such as the specific *Allium* plant used selectable agent used and specific strain of *Agrobacterium* and vector combination used. Therefore, some optimisation may be required to realise the optimal conditions, and in particular the length of time required to achieve transfer of the polynucleotide sequence, for a particular transformation. However, this could easily be achieved by a skilled person.

Following incubation with the *Agrobacterium* it is then necessary to select for those cells which have successfully been transformed. This is typically achieved by including a selectable marker gene that is co-transformed into the cell with the polynucleotide of interest. The selectable marker gene generally encodes a protein that confers resistance of some form to the transformed cell, for example resistance to an antibiotic or an herbicide. Common selectable markers can include, but are not limited to antibiotics e.g., kanamycin with resistance encoded by the nptII resistance gene, for selection in kanamycin-containing media, or hygromycin with resistance encoded by the hygromycin phosphotransferase gene, for selection in media containing hygromycin B; herbicides e.g. glyphosate with resistance encoded by for example the cp4 gene, or phosphinothricin with resistance encoded by for example the bar gene. Many selection markers are known in the art and any form of a selection system could be used without departing from the scope of the present invention. A general review of potential selection markers can be found in Wilmink and Dons (1993) and more specifically for *alliums* Eady and Hunger 2008.

The leaf sections are then incubated in the presence of the particular selection medium in accordance with the selection marker being used. The total length of time required for incubation with the selection medium can vary also, but should be sufficient to obtain a population of transformed *Allium* leaf cells. The selection medium may also include an agent, for example an antibiotic such as timentin, to kill any remaining *Agrobacterium*.

The transformed *Allium* leaf cells can then be used to generate a transformed *Allium* plant if so desired. The regeneration of full plants from leaf tissue is known. Briefly, the transformed cells are cultured on a regeneration medium (for example Eady et al 2000) containing a cytokinin preferably kinetin or 4FPA, or Zeatin, or combination of cytokinins and auxin, which stimulates the generation of multiple shoot buds. The shoot buds are then transferred to a medium without growth regulator (e.g. MS medium ½ level of sugar) or a medium with low concentration of auxin for further elongation of shoot and the induction and growth of roots to obtain plantlets. It will be appreciated that depending on the particular *Allium* plant used, some optimisation of appropriate cytokinins, concentrations and length of times will be required in order to regenerate an *Allium* plant. Such optimisation procedures are well known and routinely performed in any transformation experiment.

As shown in the examples, transformation of onion, garlic, spring onion and leek have successfully been achieved using the method of the present invention. Therefore, the method is successful in a wide variety of *Allium* plants, and therefore has applications in the transformation of any *Allium*, but in particular *Allium cepa, Allium fistulosum* or *Allium ampeloprasum, Allium ascalonicum, Allium schoenoprasum Allium sativum*.

The present invention also provides for an *Allium* plant transformed according to the method of the present invention. In particular, the *Allium* is *Allium cepa, Allium* fistulosum or *Allium ampeloprasum, Allium ascalonicum, Allium schoenoprasum Allium sativum*.

It will be appreciated the method can be used to produce any desired transformed plant depending on the particular polypeptide of interest. For example the polynucleotide of interest could confer an agronomic advantage e.g. resistance to herbicides such as glyphosate and or phosphinothricin (Eady et al 2003). Resistance to fungal disease such as Allium white rot. Resistance to virus diseases such as Iris Yellow Spot Virus or the viruses responsible for garlic mosaic disease. Resistance to bacterial diseases. Resistance to insect pests such as onion maggot and or thrips. The modification of the bolting and flowering pathway by use of polynucleotide sequences that can affect florigen level, recognition or activity.

Alternatively the polynucleotide of interest could confer a quality trait advantage e.g. the overexpression or silencing of colour pathway genes or their regulators. The overexpression or silencing of sulphur pathway genes or their regulators, for example the silencing of the lfs gene through the use of lfs RNAi sequences (Eady et al 2008). The overexpression or silencing of Carbohydrate pathway genes or their regulators for example the sst1 gene or sst1 RNAi sequences.

The examples set fourth below are for the purposes of illustration and are in no way intended to limit the scope of the invention.

Example 1

Transformation Procedure

Preparation of Overnight *Agrobacterium* Cultures.
Each preparation was done in duplicate to insure a good culture for cocultivation. For each plasmid, 2 lots of 50 mls of LB were obtained and 500 ul of the appropriate *Agrobacterium* aliquots (stored at −80° C.) were added to each one. The appropriate antibiotics were then added to each flask. For PART27H-mgfp5ER (has hptII and myfp5-ER genes in t-DNA) 50 ul of Spectinomycin (100 mg/ml stock) and Streptomycin (100 mg/ml stock) was added to each flask. These flasks were then placed on a shaker at 28° C. overnight.

Clove Sterilization.
Garlic bulbs were broken up into individual cloves and the outer skin was then removed from these. From each clove the underside of the basal plate from where the roots emerge was cut back using a scalpel blade to clean tissue. The cloves were then placed in glass agee jars and briefly rinsed in ddH$_2$O. The ddH$_2$O was discarded and the cloves were then covered in 70% Ethanol and washed for about 30 seconds. While the cloves were washing in alcohol, a 30% bleach solution (30% commercial bleach with 2 drops between 20 per 100 ml) was prepared. The alcohol solution was then discarded and the cloves were briefly rinsed with some of the 30% bleach solution which was then discarded. The cloves were then immersed in the remaining bleach solution. The agee jars were then placed on a shaker for 30 minutes at room temperature.

Preparation of *Agrobacterium*.
The *Agrobacterium* were removed from the 28° C. shaker and replenished with LB (1:1) (50 mls of LB was added to the *Agrobacterium* and swirled before 50 mls of this dilute solution was tipped back into the empty conical flask). The antibiotics were also replenished by adding half the aliquot initially added to the overnight culture. For PART27H-mgfp5ER (has hptII and myfp5-ER genes in t-DNA) this was 25 μl of Spectinomycin (100 mg/ml stock) and Streptomycin (100 mg/ml stock). Then, 10 μl of acetosyringone stock (500 mM in DMSO) was added to give a final concentration of 0.1 mM. These flasks were then put back on the 28° C. shaker for at least 3 hours.

Washing of Cloves.
After the cloves had been on the shaker in the bleach solution for 30 minutes, this solution was discarded and the cloves were rinsed four times with sterile water.

Organization of Equipment.
400 μl of either liquid P5 media was dispensed into sterile eppendorfs. Laminar flow hoods were switched on and sterilized. Microscopes and light source were obtained, tools were sterilized and sterile petri dishes were obtained also. P5 plates were taken out of the fridge and opened up in the back of a laminar flow hood to dry.

Isolation of Immature Leaf Sections.
The garlic cloves were cut horizontally about 1 cm above the basal plate and the top section was discarded. The remaining storage leaf and some of the largest outer most immature leaves were then excised and discarded. The remaining leaf tissue was sliced horizontally from the clove to create thin leaf sections. Leaf sections from either one to three cloves (depending on clove size) were placed in each eppendorf containing 400 ul of liquid P5.

Preparation of *Agrobacterium*.

After at least 3 hours (once all the leaf sections had been isolated) the *Agrobacterium* were removed from the 28° C. shaker. An aliquot of this *Agrobacterium* was transferred to a 50 ml falcon tube and centrifuged at ~4000 rpm (3220×g) for 5 minutes. The supernatant was then poured off and discarded. The pellet was then resuspended in either liquid P5 to give an OD of between 0.7 and 0.9 when reading the absorbance at 550 nm. Acetosyringone stock solution (500 mM in DMSO) was added to this solution at a rate of 0.8 ul/ml to give a final concentration of 0.4 mM.

Infection of Leaf Sections.

400 μl of *Agrobacterium* solution was added to each eppendorf containing leaf sections. These tubes were then vortexed for 30 seconds, after which any leaf sections that had stuck up the sides of the tubes or on the lid were flicked down so as to be immersed in solution. The lids of each eppendorf were then pierced with a scalpel blade and placed in a vacuum chamber at 25 inch Hg for 30 minutes.

Plating Out of Infected Leaf Sections.

After the vacuum treatment, the *Agrobacterium* solution was pipetted out of the eppendorfs containing the leaf sections. These leaf sections were then gently scraped into a sterile petri dish containing two pieces of sterile filter paper (Whatman 1 90 mm Diameter). Each leaf section was then carefully separated and both cut edges were blotted on the filter paper. This was performed under the microscope. When all explants had been blotted dry they were transferred to a petri dish containing solid P5. The plates were then kept at room temperature in the dark in a cupboard in the culture room for 5 days.

Subbing.

After the leaf sections had been incubated for 6 days on P5 media they were subbed onto P5/4FPA (see table below) media containing selection agents. Leaf sections infected with PART27H-mgfp5ER (has hptII and myfp5-ER genes in t-DNA) were first placed onto P5/4FA media containing Timentin 200 mg/L and Hygromycin 5 mg/L. After 3 weeks on this media leaf sections were subbed onto P5+4FPA media containing Timentin 200 mg/L and Hygromycin 10 mg/L. These leaf sections were then subbed on this media every 3 weeks until they had spent 12 weeks on selection media. During this period leaf sections remained in the dark at room temperature.

GFP Screening.

Leaf sections that had been infected with PART27H-mgfp5ER (has hptII and myfp5-ER genes in t-DNA) were screened under a blue light microscope for GFP expression (FIG. 15) before being subbed onto new media. Any material not expressing GFP was discarded. Some leaf explants were cut into smaller sections during this period to enable more complete contact with the selection media.

TABLE media composition of P5/4FPA with selective agents shown for addition after autoclaving depending on selectable marker gene used.

| STOCK SOLNS | STOCK CONC | Amount for 1 L |
|---|---|---|
| BDS Macro | 20× | 50 ml |
| BDS Micro | 200× | 5 ml |
| BDS (modified) Vits | 200× | 5 ml |
| Casein Enzymatic Hydrolysate | 50 mg/l | 50 mg |
| 4-FPA | 8.5 mg/ml (5 mM) | 1 ml |
| Sucrose (3%) | 30 g/l | 30 gm |
| Final Volume | | 1000 ml |
| Initial pH | | |
| Final pH | | 6 |
| Agar: Gelrite | | 4 gm |
| Containers | 1 L Duran Flask | |
| After Autoclaving | | |
| Glyphosate (Gly 0.05) | 0.1 M | 500 ul |
| Timentin (T200) | 300 mg/ml | 670 ul |
| Timentin (T250) | 300 mg/ml | 830 ul |
| Geneticin (G12) | 50 mg/ml | 240 ul |
| Hygromycin (H5) | 50 mg/ml | 100 ul |
| Hygromycin (H10) | 50 mg/ml | 200 ul |

Shoot Regeneration.

Once the leaf section explants had been on the selection media for 12 weeks they were transferred to SM4 media containing the appropriate antibiotics. For explants transformed with PART27H-mgfp5ER (has hptII and myfp5-ER genes in T-DNA) this was 150 mg/L Timentin and 5 mg/L Hygromycin. At this point nodular growths produced on the leaf explants were broken up (FIGS. 15 & 16). Any tissue derived from a single explant was grouped together and defined by its plate number and a letter to avoid any duplication of transformation events.

Root Regeneration.

GFP expressing tissue was then observed for the production of shoots. Once a nice shoot had been formed this was transferred onto ½ MS30 media containing the correct antibiotics for the corresponding treatment to induce root formation (FIG. 16).

Exflasking Plants.

Rooted shoot culture were washed in water to remove excess agar and then transplanted out with potting mix in a contained glasshouse facility in the spring.

Example 2

Green Florescent Protein

TABLE 1

Summary of putatively transgenic garlic lines expressing a GFP reporter gene. The gfp reporter gene came from the SpeI fragment of binary vector pBINm-gfp5-ER (provided by J. Hasseloff, Department of Plant Sciences, University of Cambridge,UK) which was inserted into the SpeI site of the pART27 binary vector (Gleave 1992)

| | Experiment No | Line No | Construct | Plant in Green House | PCR result for GFP | lab-book ref for |
|---|---|---|---|---|---|---|
| 1 | 0629 | 10 (A) | pART27H-mGFP5-ER | ✓ | + | 110965 |
| 2 | 0629 | 14 (A) | pART27H-mGFP5-ER | ✓ | + | 110965 |

TABLE 1-continued

Summary of putatively transgenic garlic lines expressing a GFP reporter gene.
The gfp reporter gene came from the Spe1 fragment of binary vector pBINm-gfp5-ER
(provided by J. Hasseloff, Department of Plant Sciences, University of Cambridge,UK)
which was inserted into the Spe1 site of the pART27 binary vector (Gleave 1992)

| Experiment No | Line No | Construct | Plant in Green House | PCR result for GFP | lab-book ref for |
|---|---|---|---|---|---|
| 3  | 0629 | 16 {C} | pART27H-mGFP5-ER | ✓ | + | 110965 |
| 4  | 0629 | 21 (B) | pART27H-mGFP5-ER | ✓ | + | 110967 |
| 5  | 0630 | 6 (A)  | pART27H-mGFP5-ER | Dead | + | 110967 |
| 6  | 0631 | 2 (G)  | pART27H-mGFP5-ER | ✓ | + | 110965 |
| 7  | 0631 | 2 (M)  | pART27H-mGFP5-ER | ✓ | + | 110965 |
| 8  | 0631 | 2 {C}  | pART27H-mGFP5-ER | ✓ | + | 110965 |
| 9  | 0631 | 3 {C}  | pART27H-mGFP5-ER | ✓ | + | 110965 |
| 10 | 0631 | 5 (A)  | pART27H-mGFP5-ER | ✓ | + | 110965 |
| 11 | 0631 | 5 (G)  | pART27H-mGFP5-ER | ✓ | + | 110965 |
| 12 | 0631 | 7 (B)  | pART27H-mGFP5-ER | | | |
| 13 | 0631 | 8 (A)  | pART27H-mGFP5-ER | ✓ | + | 110965 |
| 14 | 0631 | 8 (B)  | pART27H-mGFP5-ER | ✓ | + | 110965 |
| 15 | 0631 | 8 (I)  | pART27H-mGFP5-ER | ✓ | + | 110965 |
| 16 | 0631 | 8 (K)  | pART27H-mGFP5-ER | ✓ | + | 110965 |
| 17 | 0631 | 8 (M)  | pART27H-mGFP5-ER | ✓ | + | 110965 |
| 18 | 0631 | 11 (A) | pART27H-mGFP5-ER | ✓ | + | 110965 |
| 19 | 0631 | 11 (B) | pART27H-mGFP5-ER | ✓ | + | 110965 |
| 20 | 0631 | 11 (E) | pART27H-mGFP5-ER | ✓ | + | 110965 |
| 21 | 0631 | 11 (H) | pART27H-mGFP5-ER | | | |
| 22 | 0631 | 17 (A) | pART27H-mGFP5-ER | | | |
| 23 | 0631 | 17 (B) | pART27H-mGFP5-ER | ✓ | + | 110965 |
| 24 | 0631 | 17 (F) | pART27H-mGFP5-ER | ✓ | + | 110967 |
| 25 | 0631 | 17 (H) | pART27H-mGFP5-ER | ✓ | + | 110965 |
| 26 | 0631 | 17 (I) | pART27H-mGFP5-ER | ✓ | + | 110965 |
| 27 | 0631 | 17 (N) | pART27H-mGFP5-ER | ✓ | + | 110965 |
| 28 | 0631 | 18 (A) | pART27H-mGFP5-ER | ✓ | + | 110965 |
| 29 | 0631 | 18 (B) | pART27H-mGFP5-ER | ✓ | + | 110965 |
| 30 | 0631 | 18 (F) | pART27H-mGFP5-ER | ✓ | + | 110965 |
| 31 | 0631 | 18 (I) | pART27H-mGFP5-ER | ✓ | + | 110965 |
| 32 | 0631 | 18 (K) | pART27H-mGFP5-ER | ✓ | + | 110965 |
| 33 | 0631 | 18 (N) | pART27H-mGFP5-ER | ✓ | + | 110965 |
| 34 | 0631 | 18 (Q) | pART27H-mGFP5-ER | ✓ | + | 110965 |
| 35 | 0631 | 19 (A) | pART27H-mGFP5-ER | ✓ | + | 110965 |
| 36 | 0631 | 20 (A) | pART27H-mGFP5-ER | ✓ | + | 110964 |
| 37 | 0631 | 20 (B) | pART27H-mGFP5-ER | ✓ | + | 110964 |
| 38 | 0631 | 20 (E) | pART27H-mGFP5-ER | ✓ | + | 110964 |
| 39 | 0631 | 20 (F) | pART27H-mGFP5-ER | ✓ | + | 110964 |
| 40 | 0631 | 21 (A) | pART27H-mGFP5-ER | ✓ | + | 110964 |
| 41 | 0631 | 21 (B) | pART27H-mGFP5-ER | ✓ | + | 110964 |
| 42 | 0631 | 21 (C) | pART27H-mGFP5-ER | ✓ | + | 110964 |
| 43 | 0631 | 22 (B) | pART27H-mGFP5-ER | ✓ | + | 110964 |
| 44 | 0631 | 23 (A) | pART27H-mGFP5-ER | ✓ | + | 110964 |
| 45 | 0631 | 24 (B) | pART27H-mGFP5-ER | ✓ | + | 110964 |

Southern Analysis

To confirm the transgenic nature of the *allium* plants Southern analysis was performed by probing digested genolic DNA with the gfp gene probe (FIG. 2). As HindIII cuts the T-DNA only once it was possible to show copy number from the Southern analysis. 3 of the 25 transformants shown have single copies (lanes 1 & 11 2a, and 4, 2b). The other transformants have multiple copies.

Extension to Other *Allium* Species

The transformation example described above can be used with other crop *Allium* species, including *Allium cepa* (onion), *fistulosum* (spring onion) and *ampeloprasum* (Leek). FIGS. 3-14 below show that the described process of transformation produces identical initial GFP gene transfer expression patterns in young (immature) leaf material of onion (*Allium cepa*) and spring onion (*Allium fistulosum*) leek (*Allium ampeloprasum*) species and that culturing such tissue can easily produce shoot cultures (FIGS. 8,12, 14).

Example 3

Fungal Resistance

Garlic leaf tissue is transformed by the method as described in Example 1. A T-DNA sequence containing a hygromycin resistant selectable marker gene, the gfp reporter gene and a oxalate oxidase (oxoxo) gene construct (FIG. 17a) was utilised.

Following transformation the plant is regenerated (FIG. 17b) on regeneration media containing hygromycin (as described above) that exhibits GFP expression (FIG. 17c) Oxalate oxidase activity of this tissue is demonstrated by histochemical staining (Simmonds et al. 2004) (FIG. 17d). PCR analysis of the genomic DNA from these plants demonstrates presence of the gene construct (FIG. 19e).

Enzymes such as oxalate oxidase or oxalate decarboxylase are potent antifungal agents against oxalate producing fungi such as *Sclerotium* species (Bidney et al (1999) (e.g. *S. cepivorum* the casual agent of allium white rot). The transfer of this gene and its activity is a demonstration of the applicability of the method of the present invention to produce fungal resistant *allium* plants.

Example 4

Viral Resistance

Garlic leaf tissue is transformed by the method as described in Example 1. A T-DNA construct containing a hygromycin resistant selectable marker gene, a gfp reporter gene and a RNAi silencing sequence directed against a consensus part of the coat protein sequence of the onion yellow dwarf virus (OYDV) and leek yellow streak virus (LYSV) respectively to confer resistance to garlic mosaic disease (FIG. 18a) was utilised.

Whole plants (FIG. 18b) were generated using the methods described above and shown to exhibit GFP expression (not shown). PCR analysis demonstrates the presence of the hyg, gfp and RNAi sequences (FIG. 18c).

The invention describes a repeatable transformation system for *allium*. The regenerating primary transformants appear to be phenotypically normal. The GFP expression, as a visual selectable marker, enabled post transformation selection conditions to be optimised. The GFP marker has also proved useful in the selection of transgenic plants from other species that are difficult to transform (Vain et al. 1998). Selection conditions have now been established, which enable the identification of transformants solely on their ability to root in selective media.

This method of producing transgenic *alliums* is repeatable and efficient. It takes a short time to produce transgenic plants and utilizes techniques that can work at high frequencies (34 transgenic plants from tissue from 8 cloves equals 350% transformation frequency) compared to previous methods which at best produced events at low frequency (12 independent events from 440 immature embryos equals 2.7%, Eady et al 2000).

It is to be understood that the scope of the invention is not limited to the described embodiments and therefore that numerous variations and modifications may be made to these embodiments without departing from the scope of the invention as set out in this specification. This is particularly applicable to modifications of media and selection conditions which could be changed by one skilled in the art without departing from the scope of the invention. Also the types of genes or DNA sequences that can be inserted is not limited to those specifically disclosed in the specification as these could be altered without departing from the scope of the invention.

INDUSTRIAL APPLICABILITY

The invention provides a novel method of transforming plants of the genus *Allium* and in particular garlic and onion plants. Also provided are plants transformed by the method. This allows *Allium* crop species which are an economically important vegetable species to be transformed by a variety of genes for improvement of *Allium* crop varieties.

REFERENCES

Aswath, C. R., Mo, S. Y., et al. (2006). "*Agrobacterium* and biolistic transformation of onion using non-antibiotic selection marker phosphomannose isomerase." *Plant Cell Reports* 25: 92-99.

Barandiaran X, Dipietro A, Martin J (1998). *Plant Cell Reports* 17, 737-741.

Dommisse E M, Leung D M, Shaw M L, Conner A J (1990). *Plant Science* 69, 249-257.

BASTAR Manja-Tina, LUTHAR Zlata, BOHANEC Borut. Use of direct somatic organogenesis for *Agrobacterium*-mediated transformation of onion *Acta Biologica Slovenica*, 2003, 46: 3-7

Bidney, D. L., Charne, D. G., et al. (1999). Production of pathogen resistant plants. International, World intellectual property organization.

Eady, C. C. (1995). "Towards the transformation of onions." *New Zealand Journal of Crop and Horticultural Science* 23: 239-250.

Eady C C, Lister C E, Suo Y, Schaper D (1996). *Plant Cell Reports* 15, 958-962.

Eady C C, Suo Y, Butler R C (1998). *Plant Cell Reports* 18: 111-116.

Eady C C, Lister C E (1998a). *Plant Cell Reports* 18: 117-121:

Eady, C. C., Weld, R. J., et al. (2000). "*Agrobacterium tumefaciens*-mediated transformation and transgenic-plant regeneration of onion (*Allium cepa* L.)." *Plant Cell Reports* 19: 376-381.

Eady, C. C., Davis, S., et al. (2003a). "*Agrobacterium tumefaciens*-mediated transformation and regeneration of herbicide resistant onion (*Allium cepa*) plants." *Annals of Applied Biology* 142: 213-217.

Eady, C., Davis, S., et al. (2005). "*Agrobacterium tumefaciens*-mediated transformation of leek (*Allium porrum*) and garlic (*Allium sativum*)." *Plant Cell Reports* 24 (4): 209-15.

Eady Colin C., Takahiro Kamoi, Masahiro Kato, Noel G. Porter, Sheree Davis, Martin Shaw, Akiko Kamoi, and Shinsuke Imai (2008) Silencing Onion Lachrymatory Factor Synthase Causes a Significant Change in the Sulfur Secondary Metabolite Profile. *Plant Physiology*, August 2008, Vol. 147, pp. 2096-2106, Eady, Colin C. (Sarah A. Hunger), *Alliums*, in Kole, C. and Hall, T. C. (eds.), "Compendium of Transgenic Crop Plants: Transgenic Vegetable Crops", Blackwell Publishing, Oxford, UK, 2008, pp 185-204.

Fereol L.•V. Chovelon•S. Causse N. Michaux-Ferriere•R. Kahane (2002) Evidence of a somatic embryogenesis process for plant regeneration in garlic (*Allium sativum* L.) *Plant Cell Rep* (2002) 21:197-203

Haseloff J, Siemering K R, Prasher D C, Hodge S (1997). *Proceedings of the National Academy of Sciences of the United States of America* 94, 2122-2127.

Hong W, Debergh P (1995). *Plant Cell Tissue & Organ Culture* 43, 21-28.

Klein T M, Wolf E D, Wu R, Sanford J C (1987). *Nature* 327, 70-73.

Kondo, T., Hasegawa, H., et al. (2000). "Transformation and regeneration of garlic (*Allium sativum* L.) by *Agrobacterium*-mediated gene transfer." *Plant Cell Reports* 19: 989-993.

Saker M M (1998). *Biologia Plantarum* 40, 499-506.

Simmonds, J., Cass, L., et al. (2004). "Oxalate oxidase; a novel reporter gene for moncot and dicot transformations." *Molecular Breeding* 13(1): 79-91. stant to beet armyworm (*Spodoptera exigua* Hubner)." Molecular breeding 14: 293-307.

Vain P, Worland B, Kohli A, Snape J W, Christou P (1998). *Theoretical & Applied Genetics* 96, 164-169.

Wilmink and Dons (1993) *Plant Mol. Biol. Reptr,* 11(2): 165-185

Xue H M, Araki H, Kanazawa T, Harada T, Yakuwa T (1997). *Journal of the Japanese Society for Horticultural Science* 66, 353-358.

Zheng, S.-J., Henken, B., et al. (2001a). "Molecular characterisation of transgenic shallots (*Allium cepa* L.) by adaptor ligation PCR (AL-PCR) and sequencing of genomic DNA flanking T-DNA borders." *Transgenic Research* 10: 237-245.

Zheng, S.-J., Khrustaleva, L., et al. (2001b). "*Agrobacterium tumefaciens*-mediated transformation of *Allium cepa* L.: the production of transgenic onions and shallots." *Molecular breeding* 7: 101-115.

Zheng, S.-J., Henken, B., et al. (2004). "The development of a reproducible *Agrobacterium tumefaciens* transformation system for garlic (*Allium Sativum* L.) and the production of transgenic garlic resistant to beet armyworm (*Spodoptera exigua* Hubner)." *Molecular breeding* 14: 293-307.

The invention claimed is:

1. A method of transforming cells from an *Allium* plant species with a polynucleotide of interest comprising the steps of:
   (i) isolating a section of immature leaf from a bulb of the *Allium* plant to be transformed, wherein said immature leaf is within approximately 1.5 cm³ of the central basal plate of the bulb;
   (ii) co-culturing the section of immature leaf with *Agrobacterium* containing one or more suitable vectors comprising the polynucleotide of interest for a length of time sufficient to achieve transfer of the polynucleotide sequence of interest into one or more plant leaf cells; and
   (iii) transferring the section of immature leaf to a selection medium that allows for the selection of transformed *Allium* plant cells, wherein the *Allium* plant is any one of *Allium cepa, Allium fistulosum, Allium ampeloprasum, Allium ascalonicum, Allium schoenoprasum* and *Allium sativum*.

2. The method of claim 1, wherein the one or more vectors is a binary vector.

3. The method of claim 1, wherein the selection medium includes an agent to selectively kill the *Agrobacterium*.

4. The method of claim 1, wherein the polynucleotide of interest confers an agronomic advantage.

5. The method of claim 1, wherein the polynucleotide of interest confers a resistance selected from the group consisting of:
   (a) herbicide resistance;
   (b) fungal disease resistance;
   (c) virus resistance;
   (d) bacterial disease resistance;
   (e) resistance to insect pests; and
   (f) antibiotic resistance.

6. The method of claim 1, wherein the polynucleotide of interest confers a modification of the bolting and flowering pathway.

7. The method of claim 1, wherein the polynucleotide of interest affects florigen level, recognition or activity.

8. The method of claim 1, wherein the polynucleotide of interest confers a quality trait advantage.

9. The method of claim 1, wherein the polynucleotide of interest confers overexpression or silencing of colour pathway genes or their regulators.

10. The method of claim 1, wherein the polynucleotide of interest confers at least one of:
    (a) overexpression or silencing of sulphur pathway genes or their regulators;
    (b) the silencing of the Ifs gene through the use of Ifs RNAi sequences;
    (c) the overexpression or silencing of carbohydrate pathway genes, or their regulators, or sst1 or sst2.

11. The method of claim 1, further comprising the step of regenerating a transformed plant from the transformed cells.

12. The method of claim 5, wherein the herbicide is selected from at least one of glyphosate and phosphinothricin; the fungal disease is *Allium* white rot; the virus is at least one of Iris Yellow Spot Virus and the viruses responsible for garlic mosaic disease; the insect pest is at least one of onion maggot and thrips; and the antibiotic is kanamycin or hygromycin.

* * * * *

UNITED STATES PATENT AND TRADEMARK OFFICE
CERTIFICATE OF CORRECTION

PATENT NO.      : 8,481,813 B2                                              Page 1 of 1
APPLICATION NO. : 12/739700
DATED           : July 9, 2013
INVENTOR(S)     : Eady et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 462 days.

Signed and Sealed this
Eighth Day of September, 2015

Michelle K. Lee
*Director of the United States Patent and Trademark Office*